United States Patent
Williston

[11] Patent Number: 5,804,706
[45] Date of Patent: Sep. 8, 1998

[54] SYSTEM AND METHOD FOR MEASURING THE MAR RESISTANCE OF MATERIALS

[75] Inventor: Ralph H. Williston, Lamar, Mo.

[73] Assignee: O'Sullivan Industries, Inc., Lamar, Mo.

[21] Appl. No.: 794,325

[22] Filed: Feb. 3, 1997

[51] Int. Cl.$^6$ .................................................. G01N 3/00
[52] U.S. Cl. ........................................ 73/78; 73/7; 73/81
[58] Field of Search ................................. 73/78, 81, 104, 73/105, 862.541, 866, 7

[56] References Cited

U.S. PATENT DOCUMENTS

| | | | |
|---|---|---|---|
| 1,544,332 | 6/1925 | Mance | 73/78 |
| 2,130,269 | 9/1938 | Dietert | 73/78 |
| 2,279,264 | 4/1942 | Hoffman | 73/78 |
| 2,735,290 | 2/1956 | Macks . | |
| 2,801,540 | 8/1957 | Rondeau | 73/78 |
| 2,978,101 | 4/1961 | Secunda . | |
| 3,069,892 | 12/1962 | Gjertsen | 73/78 |
| 3,087,326 | 4/1963 | MacDonnell . | |
| 3,289,458 | 12/1966 | Deichert et al. | 73/78 |
| 3,688,556 | 9/1972 | Bigelow . | |
| 3,785,198 | 1/1974 | Heetman | 73/78 |
| 4,103,538 | 8/1978 | Stoferle et al. | 73/81 |
| 4,719,583 | 1/1988 | Takafuji . | |
| 4,791,807 | 12/1988 | Oechsle | 73/78 |
| 4,848,140 | 7/1989 | Fischer | 73/81 |
| 4,958,511 | 9/1990 | Marcus . | |
| 5,027,650 | 7/1991 | Oblas et al. | 73/78 X |
| 5,323,648 | 6/1994 | Peltier et al. | 73/78 X |
| 5,343,733 | 9/1994 | Nakagawa . | |
| 5,531,095 | 7/1996 | Hupf . | |
| 5,533,382 | 7/1996 | Clerkin . | |
| 5,563,329 | 10/1996 | Smith . | |

FOREIGN PATENT DOCUMENTS

| | | |
|---|---|---|
| 476747A | 3/1992 | European Pat. Off. . |
| 0098232 | 5/1987 | Japan . |

Primary Examiner—Elizabeth L. Dougherty
Attorney, Agent, or Firm—Haynes and Boone, LLP

[57] ABSTRACT

A system and method for measuring the mar resistance of a material test specimen includes a frame, a platform positioned on the frame, and a bar slidably mounted on the frame for vertical movement above the platform. The bar defines a lower end configured for holding a contact block at a predetermined angle relative to the platform, and an upper end configured for receiving and holding a mass of material. The test specimen is positioned on the platform, and the bar is moved downwardly toward the surface of the test specimen until the contact block comes to rest on the surface of the specimen. The specimen is then moved across the platform, the surface of the specimen is examined for mars, and the mar resistance is determined for the predetermined angle as the maximum amount of force, or pressure, which may be applied through the contact block to the surface of the specimen without marring the surface thereof.

18 Claims, 4 Drawing Sheets

SYSTEM AND METHOD FOR MEASURING THE MAR RESISTANCE OF MATERIALS

BACKGROUND OF THE INVENTION

The invention relates generally to measuring and testing devices and, more particularly, to a device for measuring the resistance of a material to the formation of a mark, abrasion, or mar on the surface of the material.

The surfaces of wood furniture, walls, and the like are finished to provide a desirable aesthetic appearance. When another piece of furniture, or any hard object fabricated, for example, from wood, metal, or the like, comes into contact with and rubs over the finished surface of the furniture, there can result on the finished surface a visible mark generally referred to as a "mar". Such a mar alters the gloss level, texture, and/or smoothness of the finished surface. The extent to which the gloss level, texture, and/or smoothness of the finished surface is changed, though, depends on the "mar resistance" of the material. It can be appreciated that, when selecting materials to fabricate articles from, it would be desirable to be able to measure a material's resistance to marring so that materials having a high mar resistance are selected.

Conventionally, the measurement of mar resistance has been estimated by abrading the finished surface of a material with a fingernail, a coin, or any object that might come into contact with the finished surface. A drawback with this method, however, is that it is very difficult to obtain repeatable, reliable data characterizing the angle at which such an object contacts the finished surface and the pressure or force that must be applied to the object at such an angle to mar the finished surface.

What is needed is a system and method for generating reliable data characterizing the resistance of a material to the formation of a mark, abrasion, or mar on the surface of the material when various objects come into contact at various angles with the surface of the material.

SUMMARY OF THE INVENTION

The present invention, accordingly, provides a system and method for generating reliable data characterizing the mar resistance of a material. To this end, the system and method of the present invention for measuring the mar resistance of a material test specimen includes a frame, a platform positioned on the frame, and a bar slidably mounted on the frame for vertical movement above the platform. The bar defines a lower end configured for holding a contact block at a predetermined angle relative to the platform, and an upper end configured for receiving and holding a mass of material. The test specimen is positioned on the platform, and the bar is moved downwardly toward the surface of the test specimen until the contact block comes to rest on the surface of the specimen. The specimen is then moved across the platform, the surface of the specimen is examined for mars, and the mar resistance is determined for the predetermined angle as the maximum amount of force, or pressure, which may be applied through the contact block to the surface of the specimen without marring the surface thereof.

An advantage achieved with the present invention is that it enables the amount of force, or pressure, needed to mar a finished surface to be precisely and reliably measured.

Another advantage achieved with the present invention is that the effect of various contact materials on the mar resistance of any surface may be determined.

Another advantage achieved with the present invention is that the effect of the angle of contact of an object on a finished surface may be determined.

Another advantage achieved with the present invention is that it enables the hardness of a finished surface to be measured by observing and measuring the indentation in the tested surface by the contact point.

Another advantage achieved with the present invention is that it allows for the shape of a contact point to be changed and the mar resistance of a finished surface to the changed contact point to be precisely measured.

DETAILED DESCRIPTION OF THE PREFERRED EMBODIMENT

Figure 1:
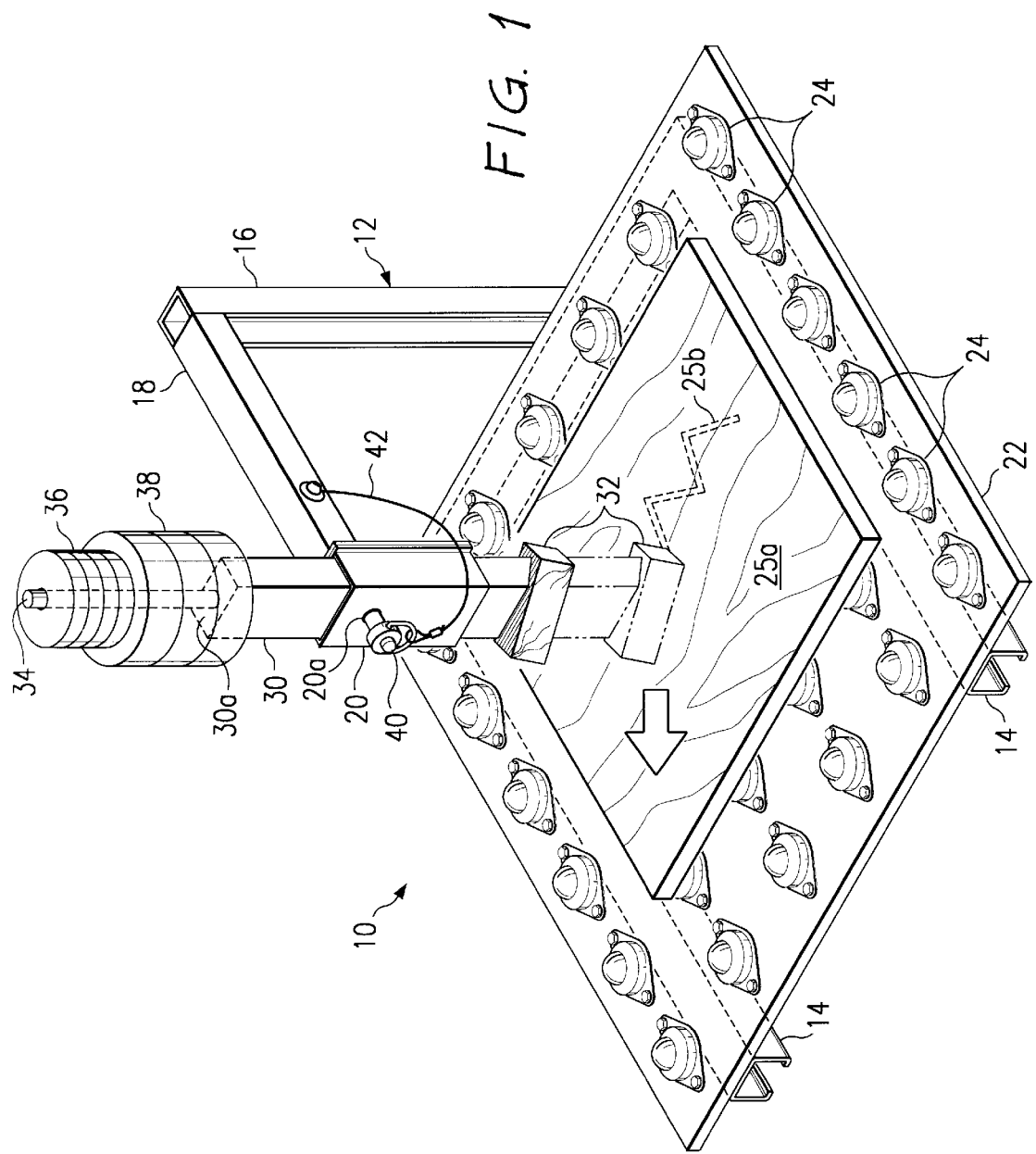
FIG. 1 is a perspective view of a device embodying features of the present invention for measuring material surface mar.
Figure 2:
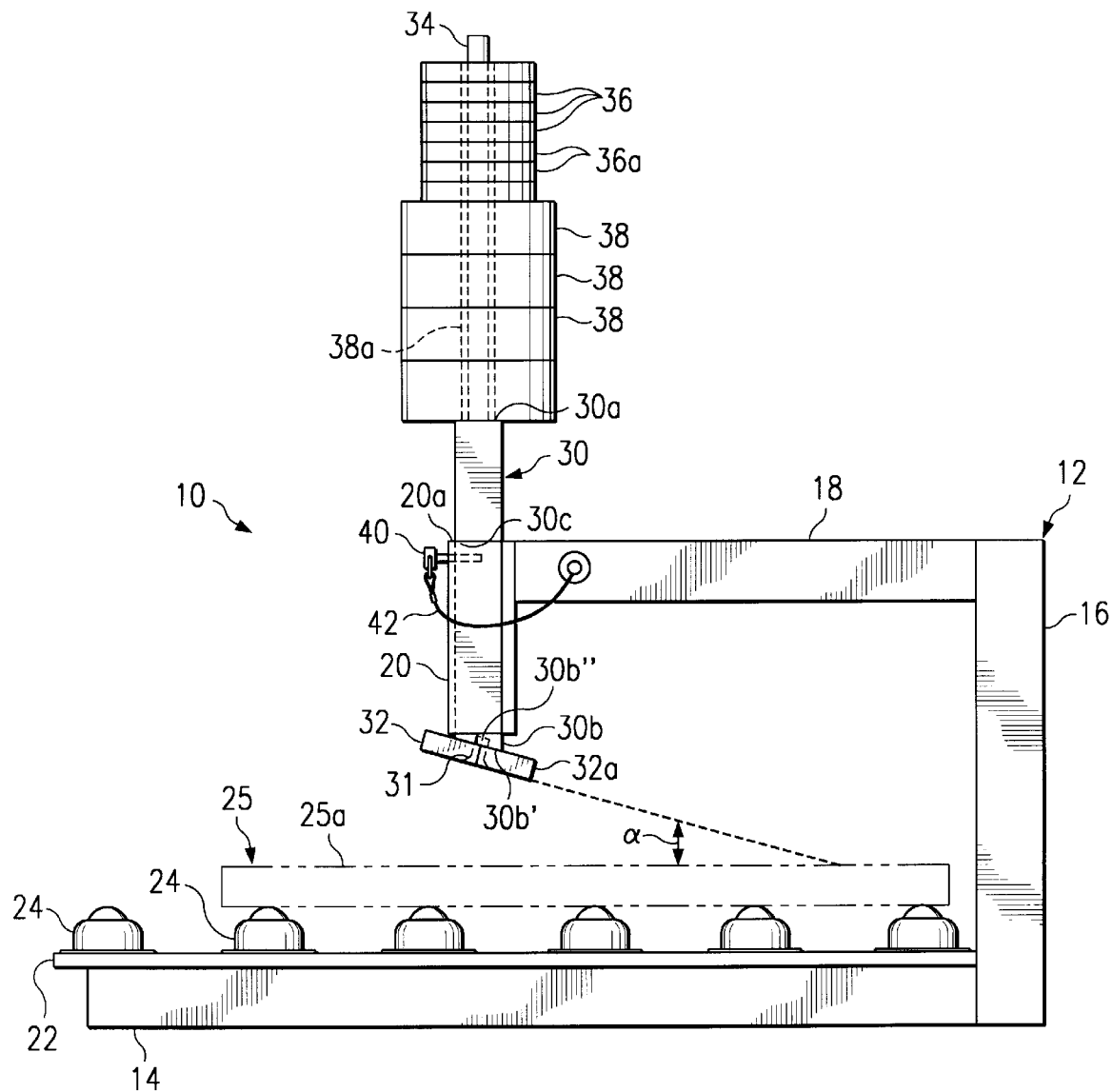
FIG. 2 is a side elevational view of the device of FIG. 1.

Referring to FIGS. 1 and 2, the reference numeral 10 designates, in general, a device embodying features of the present invention for measuring the surface mar of a material. The system 10 includes a support frame 12 having a base 14, an upright extension 16 welded to and extending upwardly from the base portion, a lateral extension 18 welded to and extending horizontally from the upright extension, and a sleeve 20 (having a rectangular cross-section) welded to and extending vertically from the lateral portion. The foregoing components of the frame 12 are preferably fabricated from steel channel beam and plate, but may also be fabricated from any suitable structural elements, such as tube (e.g., pipe), I-beam, and the like, formed from any suitable material such as steel, aluminum, and the like.

A flat aluminum roller platform 22 is preferably tack welded, or otherwise secured, to the top side of the base 14. The platform 22 may be fabricated from any suitable material, in addition to aluminum, such as steel. Preferably, thirty six or, alternatively, any desired number of, ball transfers, or ball bearings, 24, well known in the art, are mounted on the platform 22 for facilitating movement across the platform, as described below, of a material test specimen 25, having a test surface 25a, which surface is preferably a finished surface.

A steel test weight bar 30, having a rectangular cross-section, is slidably mounted within the sleeve 20 for vertical movement above the platform 22. The bar 30 includes an upper end 30a and a lower end 30b. A support rod 34 is preferably welded or, alternatively, screwed, bolted, or otherwise secured, to the upper end 30a of the bar 30. One-pound and five-pound disc-shaped masses of material, or weights 36 and 38, respectively, having bores 36a and 38a, respectively, centrally formed therein, are placed over the rod 34 so that the rod extends through the bores of the weights, and so that the weights are supported on the upper end 30a of the bar and thereby urge the bar downwardly toward the platform 22. Though not shown, the bar 30 and each of the weights 36 and 38 are marked with their respective weights.

As most clearly depicted in FIG. 2, the lower end 30b of the bar 30 defines a surface 30b' formed at a test angle α relative to the base 14. While not shown, three bars 30 are provided, having respective test angles α of 10°, 20°, and 30°. It is understood that additional bars 30 may be provided with additional test angles a as desired. A threaded bore 30b" extends through the surface 30b' for receiving a screw 31, such as a cap screw. A square contact block 32, preferably configured from a hard plastic or wood, such as oak, is secured to the lower end 30b of the bar 30 with the cap screw 31 secured in the threaded bore 30b". As viewed in FIG. 2, the contact block 32 defines a contact point 32a which is the low point of the block and which would first contact a test surface 25a of the material test specimen 25 as the test weight bar 30 is lowered.

Horizontal bores 20a and 30c are formed in the sleeve 20 and the bar 30, respectively, such that, when the two bores are aligned, the contact point 32a of the contact block 32 is elevated above the test surface 25a of the test specimen 25. A quick release pin 40 is attached to the lateral extension 18 of the frame 12 via a cable 42, and is sized for insertion through the bores 20a and 30c when the bores are aligned, thereby supporting the elevated position of the bar 30 within the sleeve 20, and maintaining the elevation of the contact point 32a above the test surface 25a.

Figure 3A:
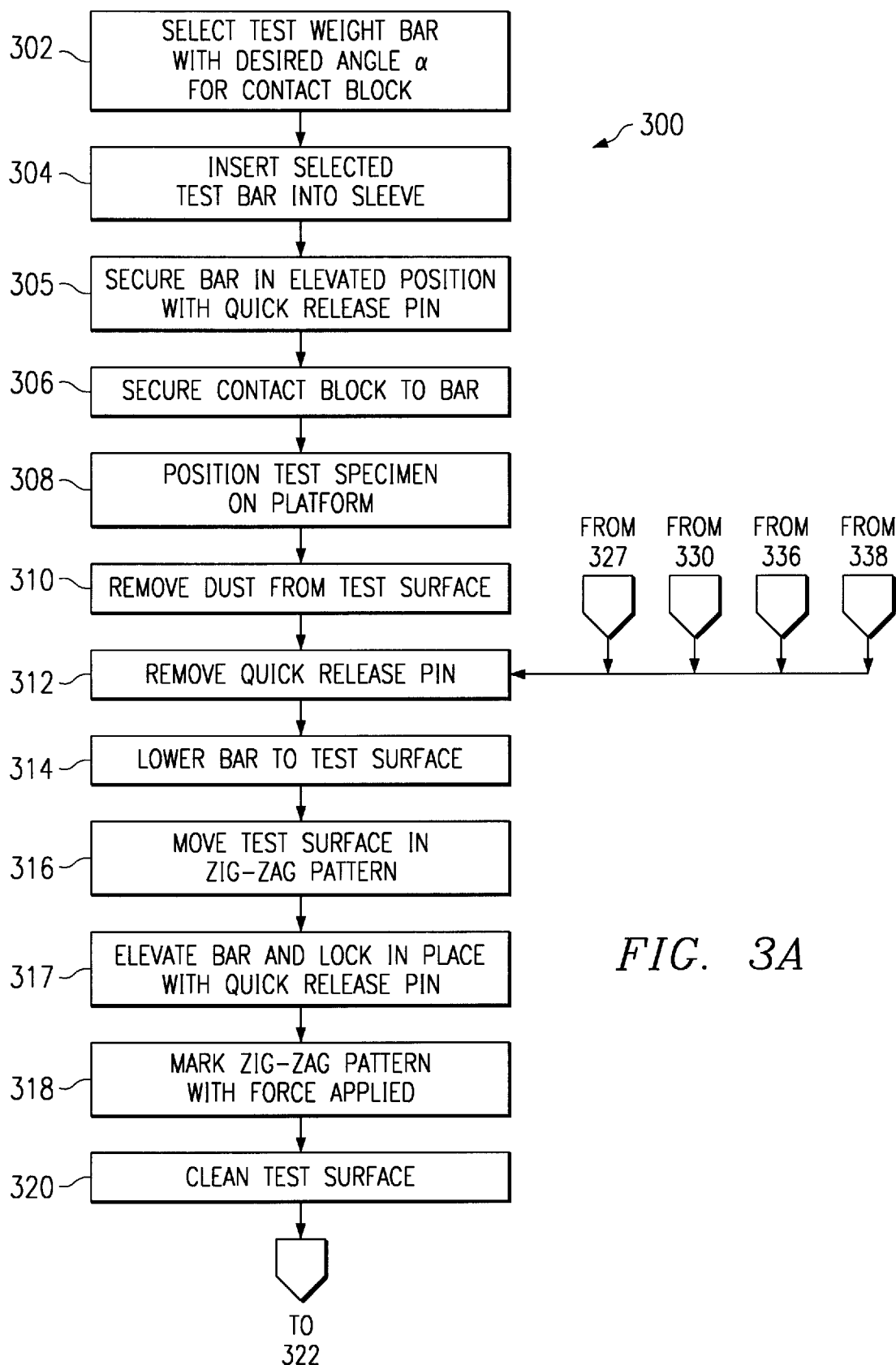
FIGS. 3A and 3B are a flow chart illustrating steps for operating the system of FIG. 1.
Figure 3B:
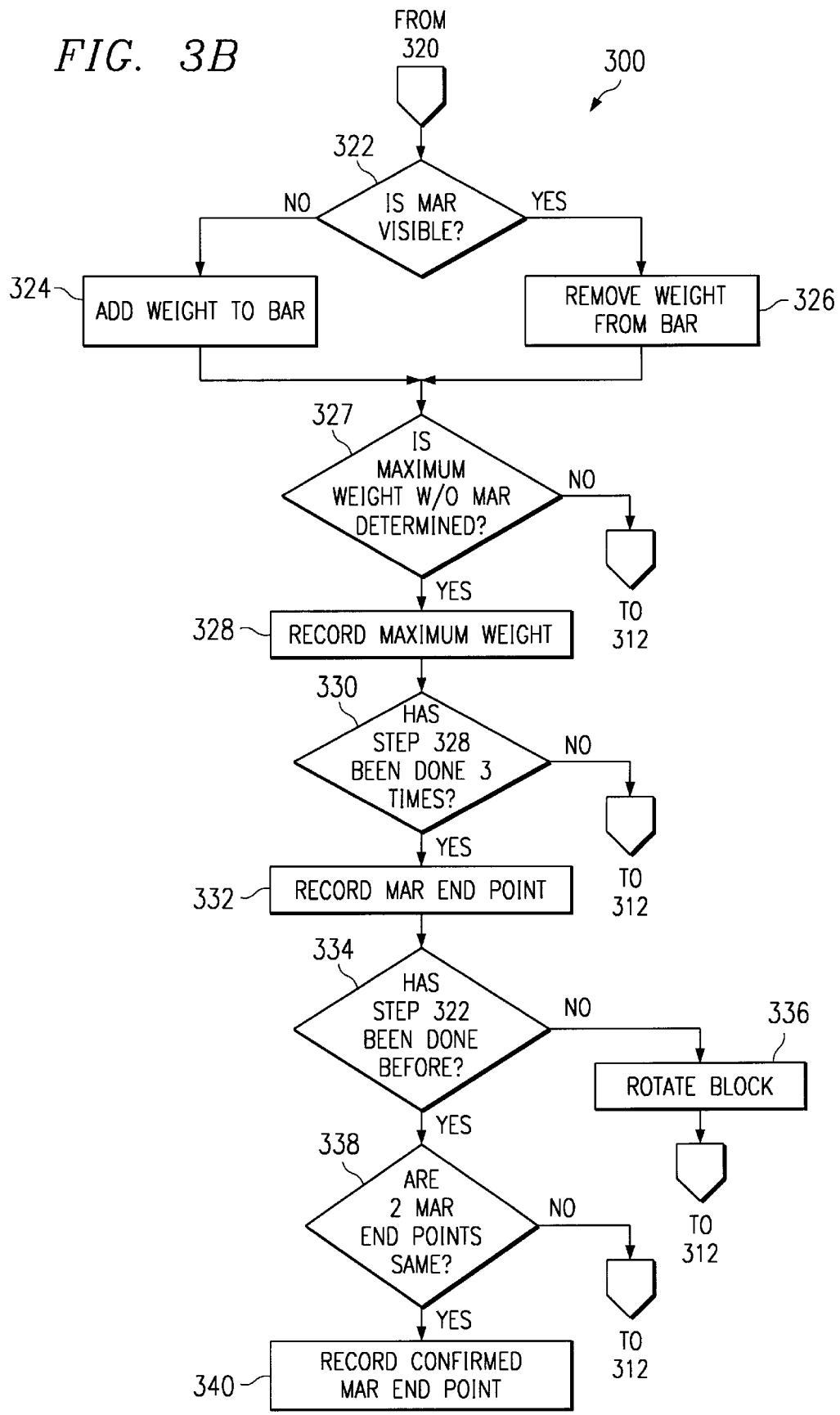

FIG. 3 is a flow chart of a method 300 depicting steps for operating the system 10 in accordance with the present invention. In step 302, a test weight bar 30 is selected having a desired test angle α through which force is to be applied through the contact point 32a to the surface 25a of the material test specimen 25. In step 304, the selected bar 30 (without weights 36 or 38) is inserted into the sleeve 20 and positioned so that the bores 20a and 30c are aligned. In step 305, the quick release pin 40 is inserted through the aligned bores 20a and 30c to secure the bar 30 in an elevated position above the roller platform 22. In step 306, the contact block 32 is secured to the surface 30b' of the bar 30 with the screw 31. In step 308, the material test specimen 25 is positioned on the roller platform 22 and, in step 310, the test surface 25a is lightly dusted off, preferably, with a soft clean cotton cloth.

In step 312, the quick release pin 40 is removed and, in step 314, the bar 30 is carefully lowered until the contact point 32a comes into contact with, and rests on, the test surface 25a. In step 316, the specimen 25 is manually and slowly moved a short distance, such as three inches, in a first direction, and then moved the same distance in a second direction lateral to the first direction. Movement of the test specimen 25 is continued, alternating between the first and second directions, thereby forming a "zig-zag" pattern 25b (FIG. 1) across the test surface 25a. In step 317, upon completion of the zig-zag pattern 25b, the bar 30 is elevated so that the bores 20a and 30c are aligned, and the quick release pin 40 is inserted through the aligned bores to secure the bar above the test surface 25a. In step 318, the zig-zag pattern 25b is marked with a writing instrument (not shown) to indicate the force applied through the contact block 32 from the weight of the bar 30 and any weights 36 and/or 38 placed on the bar.

In step 320, the surface 25a is wiped clean with a cloth and, in step 322, a determination is made whether the zig-zag pattern 25b is visible (i.e., whether the test surface 25a has been marred). If it is determined that the zig-zag pattern 25b is not visible, then, in step 324, a weight 36 or 38 is added to the upper end 30a of the bar 30. If, in step 322, it is determined that the zig-zag pattern 25b is visible, then, in step 326, a weight 36 or 38 is removed from the bar 30. By adding and removing weights in a judicious manner, it can be appreciated that, in step 327, a person having ordinary skill in the art may determine the maximum weight that can be applied through the contact block to the surface 25a of the test specimen 25 without causing a mar in the surface thereof. If, in step 327, the foregoing maximum weight is determined, then, in step 328, the maximum weight is recorded for the test specimen 25. If, in step 327, the maximum weight is not determined, then execution returns to step 312. It is understood that the weight applied through the contact point 32a is a force, and that the pressure, or stress, applied through the contact point may be calculated by dividing the applied weight, or force, by the contact area of the contact point 32a which engages the test surface 25a. The contact area and pressure (i.e., stress), as well as the test angle α, may also be recorded with the maximum weight.

In step 330, a determination is made whether step 328 has been performed three times (since the execution of step 332, described below, if it has been executed). If a determination is made that step 328 has not been performed three times, then execution returns to step 312. If a determination is made that step 328 has been performed three times, then, in step 332, the greatest of the three maximum weights recorded in each execution of step 328 is recorded as the "Mar End Point." The Mar End Point represents the maximum force that can be applied through the contact block 32 to the surface 25a of the test specimen 25 without marring the surface thereof.

In step 334, a determination is made whether step 332 has been performed more than once. If it is determined that step 332 has not been performed more than once, then, in step 336, the square block 36 is rotated 90° on the lower end 30b of the bar 30, and execution returns to step 312. If a determination is made that the step 332 has been performed more than once, then, in step 338, a determination is made whether two recorded Mar End Points are the same. If, in step 338, it is determined that two Mar End Points are not the same then execution returns to step 312. If, in step 338, it is determined that two Mar End Points are the same, then, in step 340, the Mar End Points so determined are recorded as the confirmed Mar End Point.

The present invention has several advantages. For example, the present invention enables the amount of force that will mar a finished surface to be precisely measured with repeatable results. The effect of various contact materials on the mar resistance of any finished surface may be determined. The effect of engaging the surface 25a at various test angles α with a contact block 32 until the surface is marred may be determined. The hardness of a finished surface may be measured by observing and measuring the indentation in the tested surface by the contact point. The shape of the contact point 32a may be changed and the resistance of the finished surface to the changed shape may be precisely measured.

It is understood that the present invention may take many forms and embodiments. The embodiments described herein are intended to illustrate rather than to limit the invention. Accordingly, several variations may be made in the foregoing without departing from the spirit or the scope of the invention. For example, the lower end 30b of the test weight bar 30 may be configured to enable the contact block 30 to rotate and assume various angles. The lower end 30b of the test weight bar 30 may be configured with a head to which a number of different contact blocks 32 may secured, wherein the head is rotatable for selecting an individual contact block to engage the test surface 25a, thereby providing for the test specimen 25 to be tested with different contact blocks under a predetermined amount of force, without changing the weights 36 and 38 disposed on the bar 30. The frame 12 may be configured with multiple sleeves 20 for receiving multiple test weight bars 30 so that multiple tests on the test surface 25a may be conducted simultaneously. The test surface 25a may be moved under the contact block 32 in predetermined patterns at various speeds by motorized control and mechanical linkages. Lighting may be provided to facilitate determining, in step 322, whether a mar is visible on the test surface. The contact point 32a may be configured having different shapes, such as, for example, a sharp or a round shape, and each corner of the block 32 may be provided with a different shape and the block rotated to a corner having a desired shape. The measured force applied through the contact point 32a by the test weights 36 and 38 may instead be applied through a spring arrangement or through hydraulic or gas (e.g., air) pressure cylinders.

Although illustrative embodiments of the invention have been shown and described, a wide range of modification, change, and substitution is contemplated in the foregoing disclosure and in some instances, some features of the present invention may be employed without a corresponding use of the other features. Accordingly, it is appropriate that the appended claims be construed broadly and in a manner consistent with the scope of the invention.

What is claimed is:

1. A system for measuring the mar resistance of a material test specimen, the system comprising:
   a frame;
   a platform positioned on the frame;
   a contact block for engaging the test specimen; and
   a bar slidably mounted on the frame for vertical movement above the platform, wherein the bar defines a lower end configured for holding the contact block at a predetermined angle relative to the platform so that, when the test specimen is positioned on the platform, the bar may slide downwardly toward, and the block engage and rest upon, a surface of the test specimen while the specimen is moved, relative to the contact block, across the platform.

2. The system of claim 1 wherein the surface of the test specimen is a finished surface.

3. The system of claim 1 wherein the block is a wooden block.

4. A system for measuring the mar resistance of a material test specimen, the system comprising:
   a frame;
   a platform positioned on the frame;
   a contact block for engaging the test specimen;
   a bar slidably mounted on the frame for vertical movement above the platform, wherein the bar defines a lower end configured for holding the contact block at a predetermined angle relative to the platform so that, when the test specimen is positioned on the platform, the bar may slide downwardly toward, and the contact block engages and rests upon, a surface of the test specimen while the test specimen is moved, relative to the contact block, across the platform; and
   at least one mass of material for providing weight, and wherein the bar further defines an upper end configured for receiving and holding the at least one mass of material, so that, when the block engages the surface of the test specimen, the weight of the at least one mass of material is transmitted through the bar and the contact block and is impressed upon the surface of the test specimen.

5. The system of claim 4 wherein the block is positioned so that, during engagement, only a single corner of the block contacts the surface of the test specimen.

6. A system for measuring the mar resistance of a material test specimen, the system comprising:
   a frame;
   a platform positioned on the frame and having a plurality of ball transfers for facilitating the movement of the test specimen across the platform;
   a contact block for engaging the test specimen;
   a bar slidably mounted on the frame for vertical movement above the platform, wherein the bar defines a lower end configured for holding the contact block at a predetermined angle relative to the platform so that, when the test specimen is positioned on the platform, the bar may slide downwardly toward, and the contact block engages and rests upon, a surface of the test specimen while the test specimen is moved, relative to the contact block, across the platform; and
   at least one mass of material for providing weight, and wherein the bar further defines an upper end configured for receiving and holding the at least one mass of material, so that, when the block engages the surface of the test specimen, the weight of the at least one mass of material is transmitted through the bar and the contact block and is impressed upon the surface of the test specimen.

7. A system for measuring the mar resistance of a material test specimen, the system comprising:
   a frame;
   a platform positioned on the frame;
   a contact block for engaging the test specimen:
   a bar slidably mounted on the frame for vertical movement above the platform, wherein the bar defines a lower end configured for holding the contact block at a predetermined angle relative to the platform so that, when the test specimen is positioned on the platform, the bar may slide downwardly toward, and the contact block engages and rests upon, a surface of the test specimen while the test specimen is moved, relative to the contact block, across the platform; and
   at least one mass of material for providing weight, and wherein the bar further defines an upper end configured for receiving and holding the at least one mass of material, so that, when the block engages the surface of the test specimen, the weight of the at least one mass of material is transmitted through the bar and the contact block and is impressed upon the surface of the test specimen, wherein the frame and bar define respective bores which are aligned when the bar is positioned sufficiently above the platform to prevent engagement of the block with the surface of the test specimen, and wherein the system further comprises a pin configured for insertion in the aligned bores for maintaining the position of the bar in the frame.

8. The system of claim 7 wherein the pin is a quick release pin.

9. A method for measuring the mar resistance of a test specimen, the method comprising the steps of:
   slidably mounting a bar for vertical movement in a frame, wherein the bar defines upper and lower ends;
   securing a contact block to the lower end of the bar at a predetermined angle relative to the bar;
   positioning a material test specimen, relative to the contact block, with a test surface below the contact block;
   testing the specimen, comprising the steps of:
      lowering the bar until the contact block comes into contact with and rests on the test surface of the test specimen;
      moving the test specimen, relative to the contact block, while the contact block rests on the test surface of the test specimen;

raising the bar so the contact block does not contact the test surface of the test specimen; and determining whether a mar is visible on the test surface of the test specimen;

in response to a determination that a mar is not visible, increasing the quantity of the mass of material on the upper end of the bar, and repeating the step of testing until a mar is created; and in response to a determination that a mar is visible, recording the maximum force applied through the contact block to the surface of the specimen that resulted in a determination that a mar was visible on the surface of the specimen.

10. The method of claim 9 further comprising the step of positioning at least one mass of material on the upper end of the bar.

11. The method of claim 9 wherein the steps of testing, increasing, repeating, and recording are repeated to confirm the maximum force that may be applied through the contact block to the surface of the specimen without generating a mar in the surface of the test specimen.

12. The method of claim 9 wherein the surface of the test specimen is a finished surface.

13. The method of claim 9 wherein the contact block is a wooden contact block.

14. A method for measuring the mar resistance of a test specimen, the method comprising the steps of:

slidably mounting a bar for vertical movement in a frame, wherein the bar defines upper and lower ends;

securing a contact block to the lower end of the bar at a predetermined angle relative to the bar;

positioning a material test specimen with a test surface below the contact block;

testing the specimen comprising the steps of:

lowering the bar until the contact block comes into contact with and rests on the test surface of the test specimen;

moving the test specimen in a zig-zag pattern, relative to the contact block, while the contact block rests on the test surface of the test specimen;

raising the bar so the contact block does not contact the test surface of the test specimen; and determining whether a mar is visible on the test surface of the test specimen;

in response to a determination that a mar is not visible, increasing the quantity of the mass of material on the upper end of the bar, and repeating the step of testing until a mar is created; and in response to a determination that a mar is visible, recording the maximum force applied through the contact block to the surface of the specimen that resulted in a determination that a mar was visible on the surface of the specimen.

15. The method of claim 14 wherein the step of securing a contact block further comprises positioning the block so that, when the contact block rests on the surface of the test specimen, a single corner of the block contacts the surface of the specimen.

16. A method for measuring the mar resistance of a test specimen, the method comprising the steps of:

slidably mounting a bar for vertical movement in a frame, wherein the bar defines upper and lower ends;

securing a contact block to the lower end of the bar at a predetermined angle relative to the bar;

positioning a material test specimen with a test surface below the contact block;

testing the specimen, comprising the steps of;

lowering the bar until the contact block comes into contact with and rests on the test surface of the test specimen;

moving the test specimen in a zig-zag pattern, relative to the contact block, while the contact block rests on the test surface of the test specimen;

raising the bar so the contact block does not contact the test surface of the test specimen; and determining whether a mar is visible on the test surface of the test specimen;

in response to a determination that a mar is not visible, increasing the quantity of the mass of material on the upper end of the bar, and repeating the step of testing until a mar is created; and in response to a determination that a mar is visible, recording the maximum force applied through the contact block to the surface of the specimen that resulted in a determination that a mar was visible on the surface of the specimen, wherein the step of moving further includes moving the specimen over a plurality of ball transfers.

17. A method for measuring the mar resistance of a test specimen, the method comprising the steps of:

slidably mounting a bar for vertical movement in a frame, wherein the bar defines upper and lower ends;

securing a contact block to the lower end of the bar at a predetermined angle relative to the bar;

positioning a material test specimen with a test surface below the contact block;

testing the specimen comprising the steps of;

lowering the bar until the contact block comes into contact with and rests on the test surface of the test specimen;

moving the test specimen in a zig-zag pattern, relative to the contact block, while the contact block rests on the test surface of the test specimen;

raising the bar so the contact block does not contact the test surface of the test specimen; and determining whether a mar is visible on the test surface of the test specimen;

in response to a determination that a mar is not visible, increasing the quantity of the mass of material on the upper end of the bar, and repeating the step of testing until a mar is created;

in response to a determination that a mar is visible, recording the maximum force applied through the contact block to the surface of the specimen that resulted in a determination that a mar was visible on the surface of the specimen;

after the step of mounting, the step of inserting a pin through corresponding bores formed in the bar and the frame for securing the bar in an elevated position;

before the step of lowering, the step of removing the pin; and after the step of raising, the step of reinserting the pin through corresponding bores formed in the bar and the frame for securing the bar in an elevated position.

18. The method of claim 17 wherein the pin is a quick release pin.

* * * * *